United States Patent [19]

Kramer et al.

[11] Patent Number: 5,047,952

[45] Date of Patent: Sep. 10, 1991

[54] COMMUNICATION SYSTEM FOR DEAF, DEAF-BLIND, OR NON-VOCAL INDIVIDUALS USING INSTRUMENTED GLOVE

[75] Inventors: James P. Kramer, Stanford; Peter Lindener, E. Palo Alto; William R. George, Palo Alto, all of Calif.

[73] Assignee: The Board of Trustee of the Leland Stanford Junior University, Stanford, Calif.

[21] Appl. No.: 258,204

[22] Filed: Oct. 14, 1988

[51] Int. Cl.$^5$ .............................................. G10L 5/00
[52] U.S. Cl. .................................. 364/513.5; 381/36; 340/365; 434/229
[58] Field of Search ...................... 364/513.5; 381/36; 340/365; 434/229

[56] References Cited

U.S. PATENT DOCUMENTS 4,414,537  11/1983  Grimes ................................. 340/365
4,542,291   9/1985  Zimmerman ......................... 250/231

OTHER PUBLICATIONS

Walsh & Westphal, "A Prototype Portable Electronic Speaking Aid for the Nonvocal Handicapped," IEEE Transactions on Biomedical Engineering, vol. BME-33, No. 10, Oct. 1966.
Foley, "Interfaces for Advanced Computing," Scientific American, Oct. 1987, pp. 127-135.
Tello, "Between Man and Machine," BYTE, Sep. 1988, pp. 288-293.
Kramer & Leifer, Abstract of Paper Entitled "An Expressive and Receptive Verbal Communication Aid for the Deaf, Deaf-Blind and Nonvocal Individuals," IEEE/Engineering in Medicine and Biology Society, 9th Annual Conference, Nov. 13-16, 1987.
Kramer, "The Talking Glove: A Communication Aid for Deaf, Deaf-Blind and Nonvocal Individuals," Printed 1988 as a handout, not published.
Kramer, Thesis Proposal: "N-Dimensional State Space Modeling of Hand Gestures: A Study of Automated Sign Language Translation," Mar. 23, 1987, copies given to a limited number of individuals (15).
News Article—"Invention Allows Non-Vocal to 'Talk'," The State Journal/Register, Springfield, Illinois, Nov. 15, 1987.
News Article—"'Talking' Glove Brings Hope to Deaf-Blind," The Age, Jan. 1988.
News Article—"Hand Signals Go High Tech," The London and Manchester Guardian, Aug. 31, 1988.
News Article—"'Talking' Glove Brings High-Tech Help to Deaf-Blind," Los Angeles Times, Sep. 19, 1988.
News Article—"Robot Lets the Fingers Do the Talking," New Scientist, Jun. 16, 1988.
Press Releases-Dated May 15, 1987, Assistive Device News, vol. IV, No. 1, Aug. 1987, News Release (CSUN), Oct. 6, 1987, Press Releases Cont.-Updated Press Release-Before 10/15/87, (Four Releases).

(List continued on next page.)

Primary Examiner—F. S. Kemeny
Attorney, Agent, or Firm—Henry K. Woodward

[57] ABSTRACT

A communication system for deaf, deaf-blind, or non-vocal individuals includes an instrumented glove for obtaining electrical signals indicative of a hand configuration of a first individual. Strain gage sensors in the glove flex with movement of the hand. Each sensor includes a tension strain gage and a compression strain gage which are serially connected and form two legs in a bridge circuit. Signals from the bridge circuit are amplified and digitized and applied to a computer which includes an adaptive pattern recognition algorithm which is responsive to hand-state vectors for recognizing letter beacons in hand-space. A second individual communicates with the first individual through the computer system using a portable keyboard. The output devices for communicating to the first and second individuals depend on the visual, vocal and hearing capabilities of the individuals and can be selected from a voice synthesizer, LCD monitor, or braille display.

25 Claims, 10 Drawing Sheets

OTHER PUBLICATIONS

Jespersen et al., "Joint Angle Position Sensor," (Abstract) 40th ACEMB, Niagara Falls, New York, Sep. 10-12, 1987.

Berec et al., "A Multielement Capacitive Force Sensor" (Abstract) 40th ACEMB Niagara Falls, New York, Sep. 10-12, 1987.

Soykan et al., "Signal Processing for a Force Sensor Array" (Abstract) 40th ACEMB Niagara Falls, New York, Sep. 10-12, 1987.

Marcus et al., "Sensing Human Hand Motions for Controlling Dexterous Robots," Second Annual Space Operations Automation and Robotics Workshop, Jul. 20-23, 1988.

"Hand Master Controls 'Smart' Machines," NASA Tech Briefs, p. 12, Oct. 13, 1989.

Gardner "The Power Glove," Design News, pp. 63-68, Dec. 4, 1989.

Eddy, "Power Glove Get a Grip on Your Games," Video Games & Computer Entertainment, pp. 18-20, Sep. 1989.

Orr, "Exotic CAD," Computer Graphics World, pp. 88-92, Jul. 1989.

Wright, "Altered States," Computer Graphics World, pp. 77-83, Dec. 1989.

COMMUNICATION SYSTEM FOR DEAF, DEAF-BLIND, OR NON-VOCAL INDIVIDUALS USING INSTRUMENTED GLOVE

BACKGROUND OF THE INVENTION

This invention relates generally to communication devices for deaf, deaf-blind, or non-vocal individuals, and more particularly the invention relates to a communication system which utilizes an instrumented glove.

While many deaf persons communicate effectively using a form of sign language or the fingerspelling alphabet, problems arise when a hearing person, who does not know sign language, attempts to interact with a deaf individual who does not know the "oral" method, i.e., cannot speak intelligibly and read lips. For deaf-blind persons, communication is even more difficult since they must be able to touch the hand of the person with whom they wish to interact. These communication difficulties adversely effect interpersonal relationships and vocational activities. Consequently, many deaf, deaf-blind and non-vocal people avoid situations requiring interaction with hearing persons. These disabled individuals often remain unemployed and dependent, and cannot fully participate in community life.

The most common ways a nonvocal deaf or deaf-blind person communicates with a hearing person who does not know sign language are via interpreters and notewriting. Although interpreters are effective in translating sign language or fingerspelling into speech and vice versa, they are often expensive and difficult to acquire on a moment's notice. Use of an interpreter also leads to a loss of independence and privacy. Notewriting is used by many nonvocal individuals to communicate with someone who is seated nearby, but it is awkward while walking, standing at a distance, and when more than two persons participate in a conversation.

Several communication devices, most notably the telecommunications device for the deaf (TDD) and the Telebraille, have been developed to assist individuals with hearing or speaking disabilities. While these devices are effective for telephone conversations, neither is practical as a portable, hand-held unit which could be used for personal interaction during daily encounters at such places as a store, restaurant or bank. Thus, there is a great need for a portable communication aid which would permit deaf, deaf-blind and non-vocal individuals to engage in conversation among themselves and with hearing, vocal persons.

The use of instrumented gloves in a communication system has heretofore been proposed. See U.S. Pat. No. 4,414,537 (Grimes), U.S. Pat. No. 4,542,291 (VPL Data Glove) and Foley, "Interfaces for Advanced Computing," *Scientific American*, pp. 127–135, October 1987.

The VPL glove is the only commercially available instrumented glove. The Grimes glove was made strictly to recognize fingerspelling and hence has greatly limited itself as a general-purpose instrumented glove. It relies heavily on binary contact sensors to detect finger positions, and the Grimes letter recognition algorithm requires a large lookup table stored in memory. "Hard" letter decisions are made depending on which sensing contacts are made. As previously stated, by not including a full set of analog sensors to report where each finger is located, the Grimes glove and system limits itself solely to recognition of predetermined hand formations, without provisions for monitoring of customized finger positions. Also, if a hand formation is extremely close to one of the acceptable hand formations, but one finger misses its contact sensor by 0.001", the lookup table will either choose the wrong letter or will not choose any letter at all. By including analog sensors, intelligent "soft" decisions can be made, such as when a finger does not reach desired position but is sufficiently close, the appropriate letter will still be recognized.

The VLP DataGlove does remedy several of the problems associated with the Grimes glove. The VPL glove does include a full set of analog sensors which allow the user to determine analog finger positions, not just whether or not one finger is touching another in a certain location. VPL uses a modified fiber optic wire that is designed to lose light as the wire is bent, and thus attenuate the output signal. The three main drawbacks to this sensor technology are that the sensor outputs:

1. vary nonlinearly with angle of flexure,
2. are dependent on the radius of curvature of the bend,
3. are largely coupled to neighboring sensors.

Since the sensor is nonlinear (actually $V_{out} \ae^{-b\theta}$), when the angle of flexure is doubled the output does not double. Lookup table conversions can be used to linearize $V_{out}$ vs. $\theta$, but as $\theta$ becomes larger, a change in $\theta$ produces a much smaller change in $V_{out}$. Therefore, the sensors become very insensitive for high $\theta$.

Since the VPL sensor is based on losing light as the optic wire is bent, sensor output is not only dependent on the overall angle of flexure, but more importantly (unfortunately) on the radius of curvature. For example, a very sharp, small angle may yield a higher output than a very rounded, large angle. This is a very undesirable trait because the sensors cannot be calibrated such that a certain voltage output corresponds to a certain angle of flexure because the output is also determined by how "sharp" is the person's knuckle.

Unfortunately, in addition, the VLP sensors are inherently omnidirectional sensors that not only produce output when bent along the desired axis but also produce unwanted output when a nearby finger is bent. When bent, a finger pulls slightly on the glove material attached to all neighboring sensors, causing erroneous lateral deflection and, hence, parasitic output signal.

SUMMARY OF THE INVENTION

An object of the present invention is an improved communication system for deaf, deaf-blind and non-vocal individuals.

Another object of the invention is an improved instrumented glove which senses finger positions and converts the sensed positions into data which can be utilized for computer analysis.

Still another object of the invention is a computer system which responds to sensed finger positions and controls communication output devices.

Yet another object of the invention is a communication system which is portable and readily employed by an individual.

A feature of the invention is the use of flexible strain gages in a glove to monitor the angles of finger joints.

Another feature of the invention is the use of a multiplexed Wheatstone bridge to obtain output signals indicative of strain gage flexures.

Still another feature of the invention is the use of letter beacons in "hand" state-space, or defined by the instrumented joints of a gloved hand.

Briefly, an instrumented glove, in accordance with the invention, is equipped with uniquely designed flexible sensors that monitor the angles of the finger joints. Each angle sensor consists of two long flexible strain gages mounted back to back. The gages are mounted back to back to reduce temperature sensitivity and increase signal. The strain gage assembly resides in a guiding pocket sewn over each joint. The maximum strain seen by each gage is adjusted by varying the thickness and elastic modulus of the plastic backing to which the gage is mounted. The backing thickness is selected to maximize the output signal without significantly reducing the fatigue life of the gage. The gages are wired in a Wheatstone bridge configuration that employs an analog multiplexer to select which strain gage bridge voltage is to be sampled by an analog-to-digital converter. The fingertips of the glove are preferably removed to permit the user to reliable grasp such objects as a pen or coffee cup. Material covering the middle knuckle on the palm side of the glove can also be removed to prevent binding.

A computer, which is preferably portable and carried by the user, receives the sensor data from the analog-to-digital converter and converts the data into letters and control signals based on a letter recognition algorithm. As each spelled letter is recognized, it is displayed for a sighted glove-user on an LCD display, or for a deaf-blind glove-user on a portable braille display. Spelled words are then communicated to another person by a speaker or LCD display or sent to another glover-user's LCD or braille feedback displays.

Other inputs to the computer system are provided for communicating with the glove-user. For example, a hearing person can reply to a deaf user by typing on a miniature keyboard or by voice recognition through a microphone.

The various input/output devices can be hard-wired to the computer, but the devices are preferably interconnected with the computer by an infra-red link or other non-wired transmission line.

In the letter recognition algorithm, each sensor value is treated as one component of an overall "hand-state vector," i.e., each joint angle represents one axis in an n-dimensional "hand-space" where n is the number of instrumented joints (typically n=14). As the hand moves, the hand-state vector traces a trajectory through hand-space. Initially, sensor information must be stored for each letter to inform the system of the user's fingerspelling "signature." The sets of stored sensor values are represented figuratively by "letter beacons" in hand-space. When the algorithm detects a reduced hand-state velocity, a letter formation is suspected, and the nearest beacon is determined. If the instantaneous hand-state lies within the closest beacon's predetermined n-dimensional hypersphere, or "recognition ball," the corresponding letter is recognized and placed in a word-assembly buffer. To avoid unintentional repeated recognition of the same character, hysteresis is introduced into the letter identification algorithm by requiring that the hand-state vector leave an outer hypersphere before a new character is determined. Backspacing is permitted, and a "say it" hand formation, or beacon, also exists. Once the "say it" beacon has been recognized, the entire word in the word-assembly buffer is output as synthesized speech to the hearing person via a small speaker worn by the deaf individual. When a word is spoken, the letter beacons are adaptively updated to reflect their new, most probable positions in hand-space. Continuous adaptation reduces sensitivity to ongoing variations in letter formation and sensor placement.

The invention and objects and features thereof will be more readily apparent from the following detailed description of a prototype communication system and appended claims when taken with the drawing.

DETAILED DESCRIPTION OF ILLUSTRATIVE EMBODIMENTS

Figure 1:
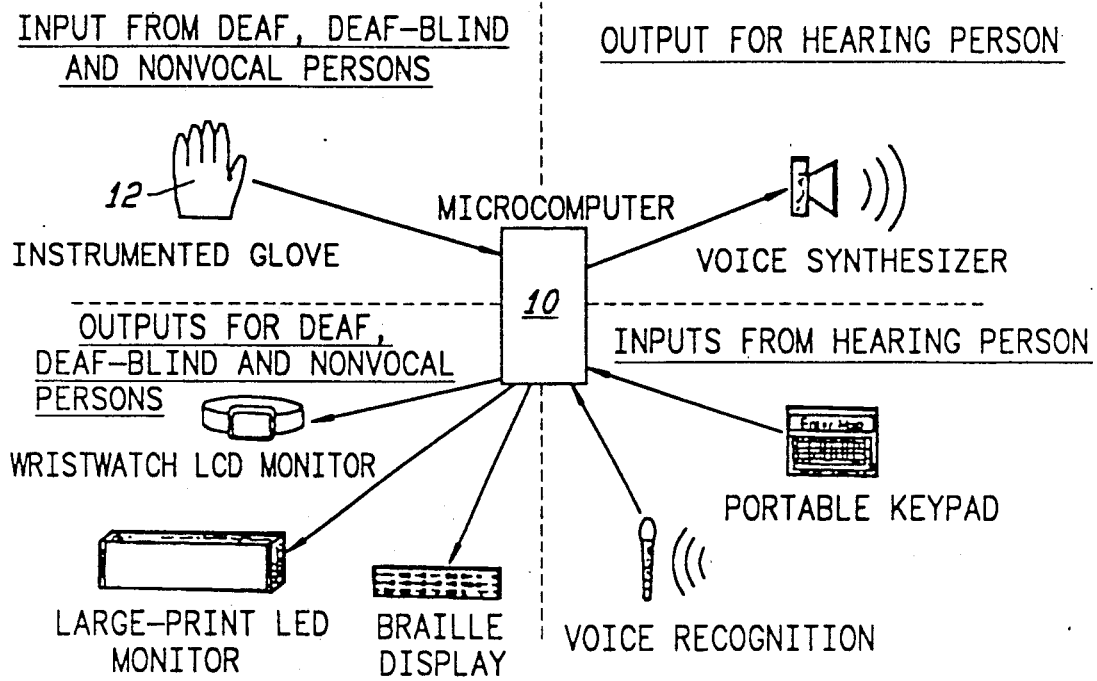
FIG. 1 is a functional block diagram of a communication system in accordance with the invention.
Figures 2A, 2B:
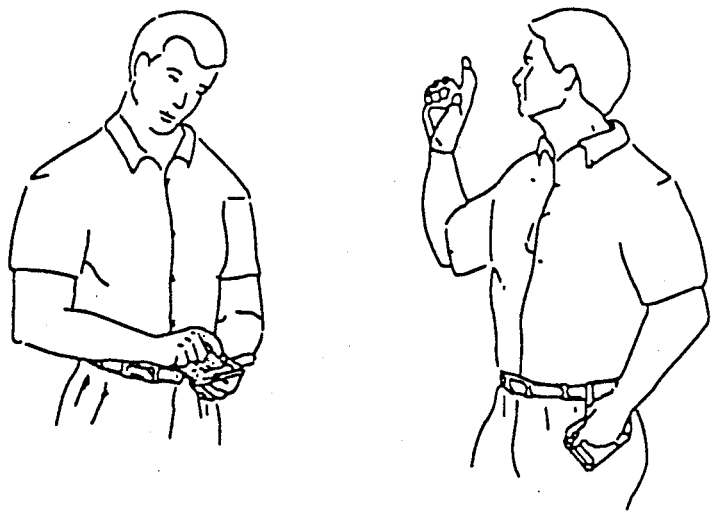
FIGS. 2A and 2B illustrate a hearing person and a deaf-blind person communicating with a communication system in accordance with the invention.

Referring now to the drawing, FIG. 1 is a functional block diagram of a communication system in accordance with the invention, and FIGS. 2A and 2B illustrate a hearing person and a deaf-blind person communicating using the system. The system provides expressive and receptive communication capabilities for deaf, deaf-blind and non-vocal persons. Although the preferred embodiment of the system be portable, as shown in FIG. 1, some components of the present prototype (FIG. 7) are too large to be carried.

The prototype system consists of a Motorola 68HC11 microcomputer board, with various interchangeable peripheral devices that encode and display information. Each user can select the peripheral devices that best satisfy his individual communication needs. In the Figures, the arrows denote the directions of information flow.

As shown in FIG. 2B, a non-vocal deaf-blind user is transmitting synthesized speech to a hearing person. The non-vocal person fingerspells while wearing a glove equipped with uniquely designed strain gage flex sensors. The microcomputer receives finger joint angle information from the instrumented glove 12 (FIG. 1), upper left). The microcomputer executes a letter recognition algorithm based o the joint angle information.

The recognition algorithm selects the most probable letter from an array of prestored hand formations that characterize the user's fingerspelling "signature." Once the letters of a word have been recognized and stored, a read-out command is given and the entire word is spoken to the hearing person (FIG. 2A) via a DECtalk speech synthesizer. The non-vocal individual wears a small output speaker (FIG. 1, upper right) as a "speech pendant" under his shirt. In effect, the non-vocal person's information output device is a "talking glove." After each word is spoken, the recognition algorithm adapts itself to reduce sensitivity to ongoing variations in letter formation and sensor placement.

A hearing person replies to the deaf user by typing on the keyboard of a Radio Shack pocket computer (FIG. 11, lower right and FIG. 2A). The keyboard has a wireless link (infra-red) to the microcomputer so it can be carried in the shirt pocket of the deaf or deaf-blind individual and handed to the hearing person. The small keyboard has a liquid crystal display (LCD) that states the deaf person's name and requests message input from the hearing individual. Data entered on this keyboard is transmitted to the microcomputer and displayed for the deaf person using one of the methods described below. It is possible for several keyboards and microcomputers to share a common communication channel so that more than one hearing individual could participate in the same conversation with more than one deaf or deaf-blind person.

An IntroVoice voice recognition system can be integrated for use in certain structured environments, such as at home or at work. Individuals trained on this system can speak directly to the deaf individual. Their speech is detected by a small, directional microphone (incorporated into the deaf person's speed pendant) and converted into text by the voice recognition equipment (FIG. 1, lower right).

Text generated by the hearing person, using either the pocket keyboard or voice recognition system, is displayed for the deaf individual in a variety of ways (FIG. 1, lower left). For sighted deaf persons, the entered message is displayed on a small Seiko LCD monitor worn like a wristwatch. For deaf persons with reduced vision, text can be output on a high-visibility, large-character LED display. For a deaf-blind user, information is presented on a specially designed mechanical braille display (FIG. 2B). The braille display can fasten to the belt for use while walking and standing but detach for desk-top use. Braille displays can also include a calculator mode, and a data-bank function to record names, phone numbers, and appointments.

Figure 3:
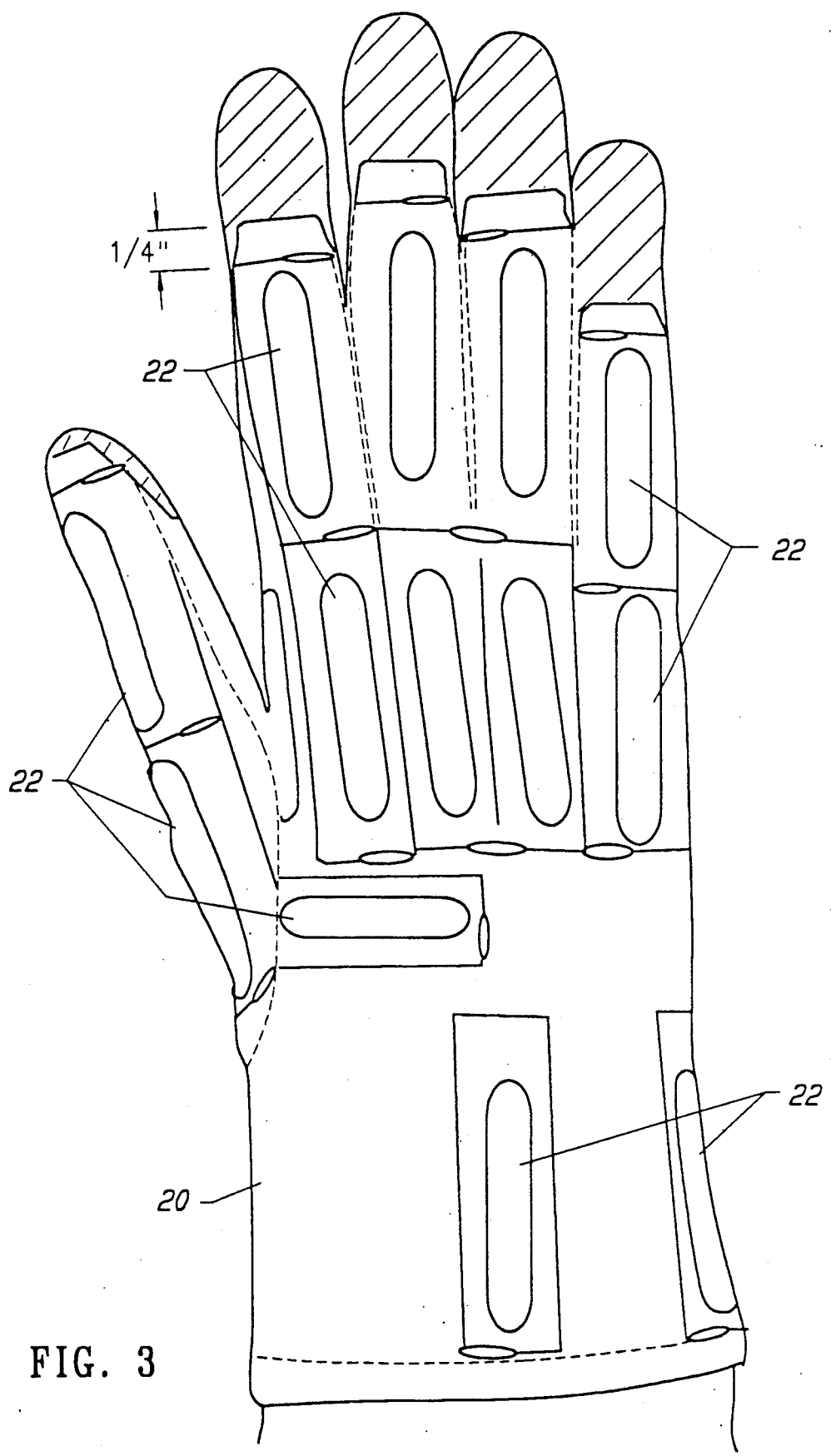
FIG. 3 is a plan view of an instrumented glove in accordance with one embodiment of the invention.
Figure 4:
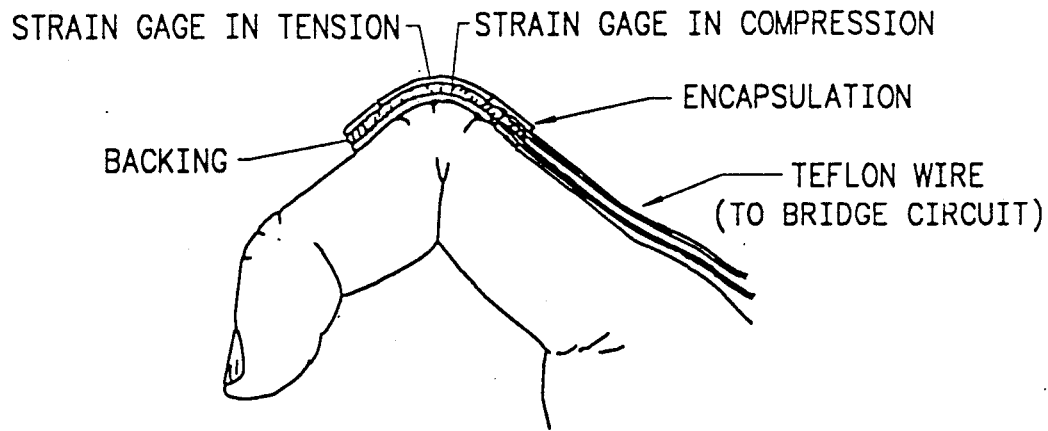
FIG. 4 is a side view of a finger joint and a strain gage flex sensor as used in the glove of FIG. 3.

FIG. 3 is a plan view of a glove 20 in accordance with one embodiment of the invention. The glove has fourteen strain gage sensors inserted into pockets 22 sewn in the glove, to sense joint flexure of the fingers while fingerspelling letters. FIG. 4 is a side view of a finger and a strain gage sensor for sensing the flexure of the finger joint. In accordance with one embodiment, two strain gage resistors are mounted on a 1 mil polyimide backing material so that during flexure, one strain gage is in tension while the other strain gage is in compression. A 120 ohm, high elongation, annealed Constantan resistor strain gage from Microengineering II (model PAH E-DF-750-120 LEN) has been used.

Data from the joint sensors is used by an adaptive pattern recognition algorithm to identify the intended letter from the fingerspelling hand formation. Recognized letters are sent to a speech synthesizer and the corresponding words transmitted as audible speech by a miniature speaker (worn as a "speech pendant" under the shirt). Common words or phrases, such as "Hello, my name is . . .," can be assigned to a single hand formation, so the entire phrase can be recognized and spoken without having to form each letter. Recognized letters and phrases can also be sent to other devices such as a TDD or computer. In effect, the user's information output device is a "talking glove."

The instrumented glove is attractive and comfortable. The fingertips and palm of the glove preferably are removed to increase functionality and ventilation. Exposed fingertips permit the user to reliably grasp such objects as a pen or coffee cup, while the open palm allows a deaf-blind person to accept manual fingerspelling. Material covering the middle knuckle on the palm side of the glove can also be removed to prevent binding. As noted above, each angle sensor consists of two long flexible strain gages mounted back to back. The strain gage assembly resides in a guiding pocket sewn over each joint. The maximum strain seen by each gage is adjusted by varying the thickness and elastic modulus of the plastic backing to which the gage is mounted. The backing thickness is selected to maximize the output signal without significantly reducing the fatigue life of the gage.

Figure 5:
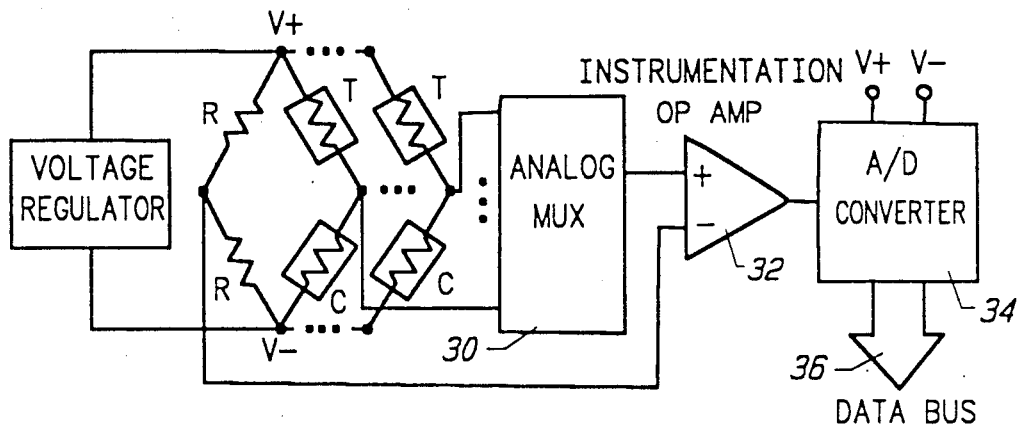
FIG. 5 is a functional block diagram schematic of a strain gage multiplexing bridge circuit for providing signals to the computer in the communication system of the invention.

The gages are wired in a Wheatstone bridge configuration that employs an analog multiplexer to select which bridge voltage is to be sampled by an analog-to-digital converter, as illustrated in FIG. 5.

Each sensor has a pair of strain gages, one in tension (T) and one in compression (C), which are used with fixed resistors (R) in a Wheatstone bridge arrangement. Each sensor bridge output is multiplexed through MUX 30 (AD7506 for example) to amplifier 32 (AD624 for example). The voltage offset of each input to MUX 30 can be varied by an offset potentiometer (not shown). The output of amplifier 32 is then applied to A/D converter 34, and the digital output from converter 34 is applied through bus 36 to the computer. The voltage range of the input to A/D converter 34 can be selected by choosing the appropriate gain of amplifier 32.

The core of the control software is an adaptive pattern recognition algorithm. In the algorithm, each sensor value is treated as one component of an overall "hand-state vector," i.e., each joint angle represents one axis in an n-dimensional "hand-space" where n is the number of instrumented joints (typically n=14). As the hand moves, the hand-state vector traces a trajectory through hand-space. This is shown for a three-dimensional space in FIG. 6.

Figure 6:
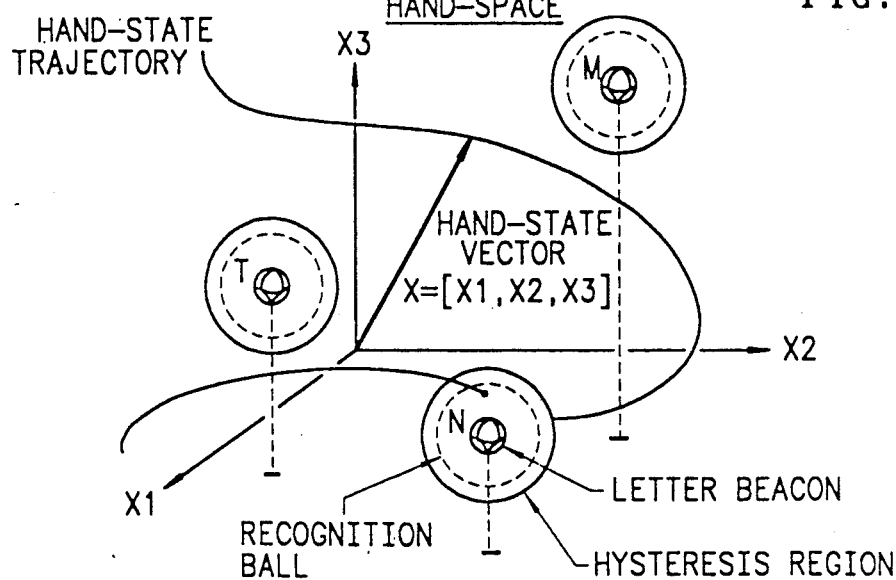
FIG. 6 is a hand-space diagram for a three-dimensional space illustrating a hand-state vector and three letter beacons as identified by a letter recognition algorithm in accordance with a feature of the invention.

Initially, sensor information must be stored for each letter to inform the system of the user's fingerspelling "signature." The sets of stored sensor values are represented figuratively by "letter beacons" in hand-space (FIG. 6). When the algorithm detects a reduced hand-state velocity, a letter formation is suspected, and the nearest beacon is determined. If the instantaneous hand-state lies within the closest beacon's "recognition hypersphere," denoted figuratively by the dashed inner spheres in FIG. 6, the corresponding letter is recognized and placed in a word-assembly buffer. To avoid unintentional repeated recognition of the same character, hysteresis is introduced into the letter identification algorithm by requiring that the hand-state vector leave the outer sphere before a new character is determined. Backspacing is permitted, and a "say it" beacon exists which, when recognized, causes the letters in the word-assembly buffer to be spoken by a DECtalk voice synthesizer. When a word is spoken, the letter beacons are adaptively updated to reflect their new, most probable positions in hand-space. Continuous adaptation reduces sensitivity to ongoing variations in letter formation and sensor placement.

Figure 7:
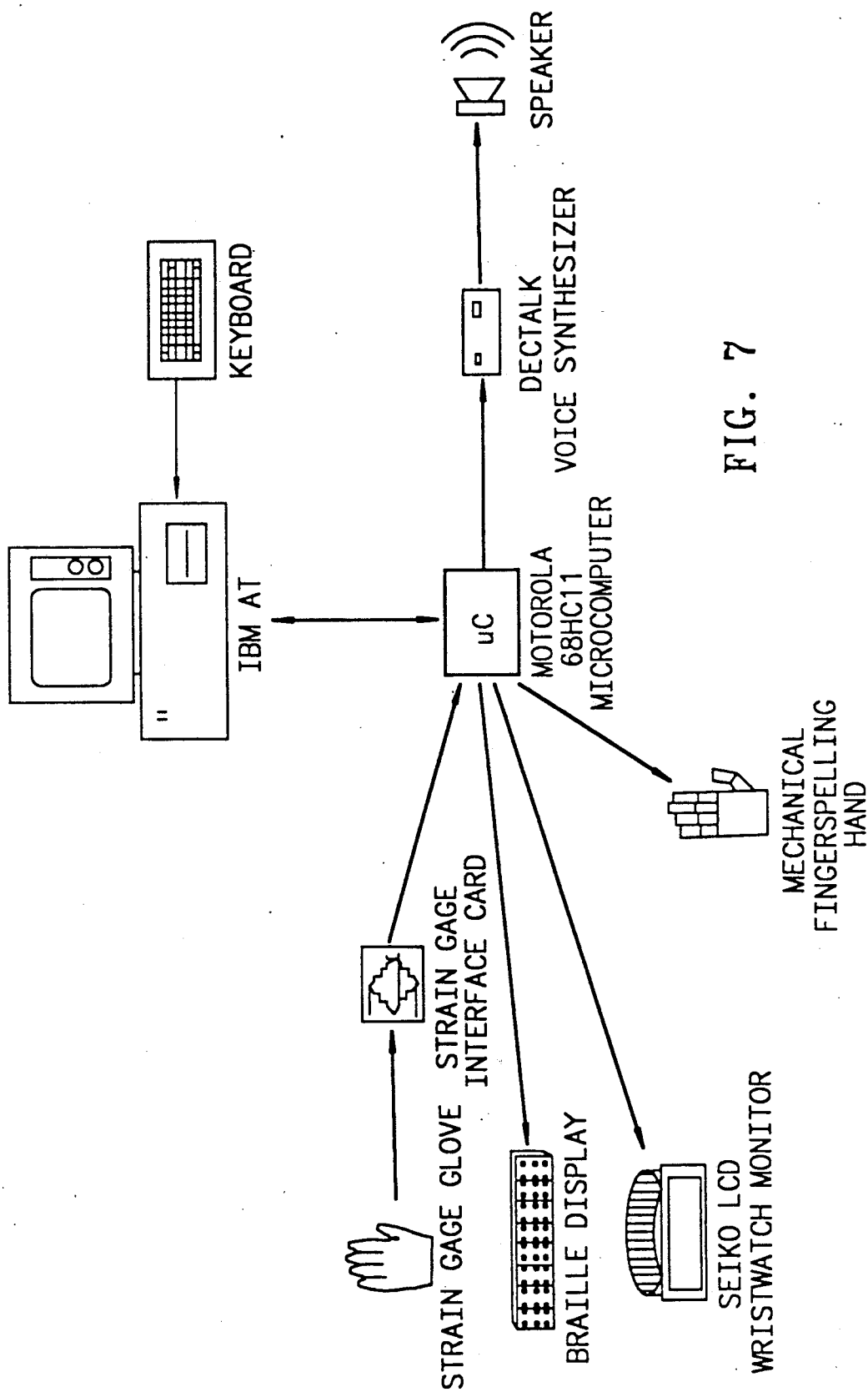
FIG. 7 is a functional block diagram of a prototype system developed at Stanford University.

FIG. 7 is a functional block diagram of a prototype communication system developed at Stanford University in which the recognition algorithm is implemented in an IBM AT personal computer. A Motorola 68HC11 microcomputer communicates with the IBM AT and also controls the operation of the peripheral devices.

Figure 8A:
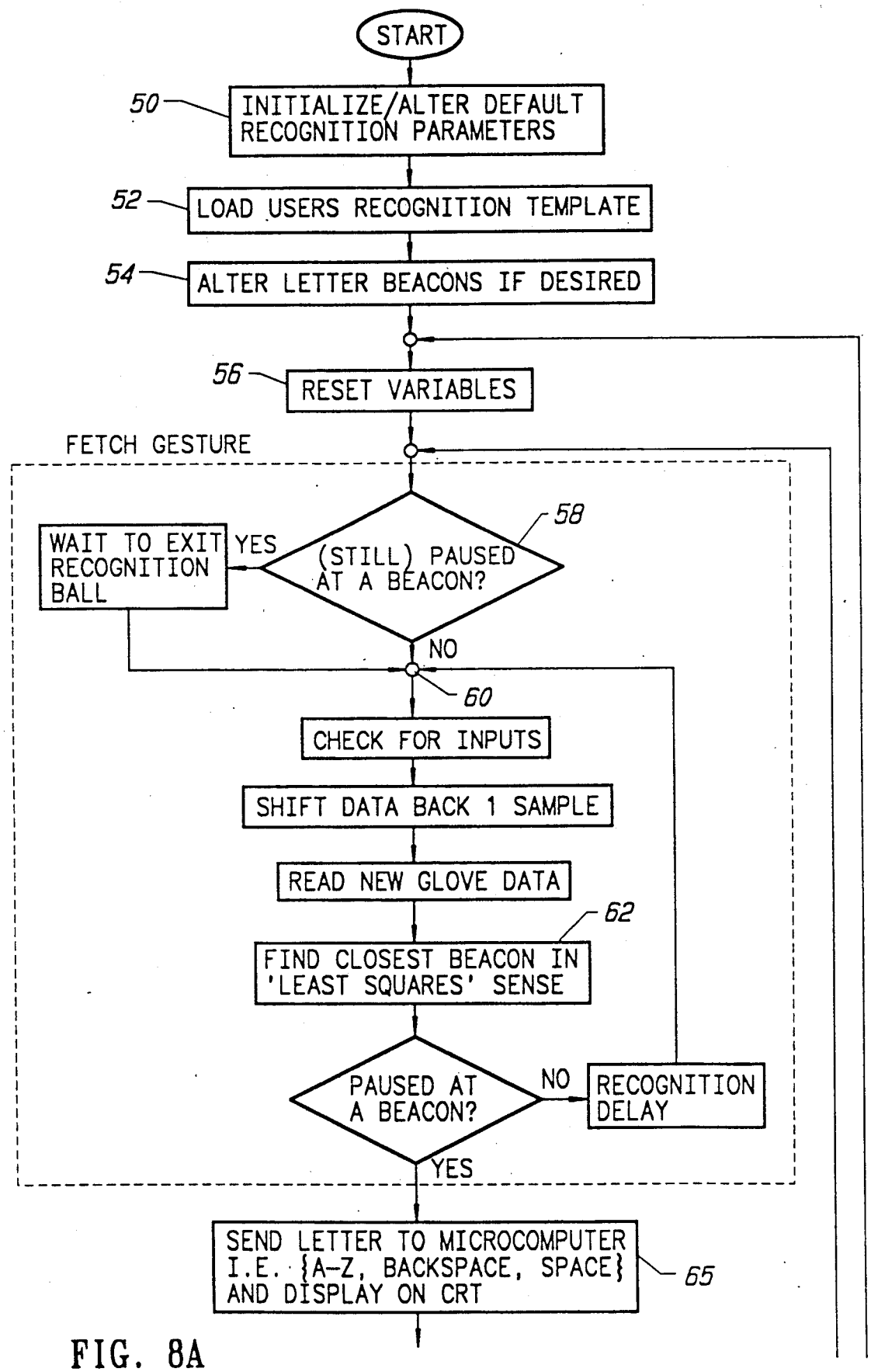
FIGS. 8A and 8B are a flow diagram of software for implementing a letter recognition algorithm in the system of FIG. 7.
Figure 8B:
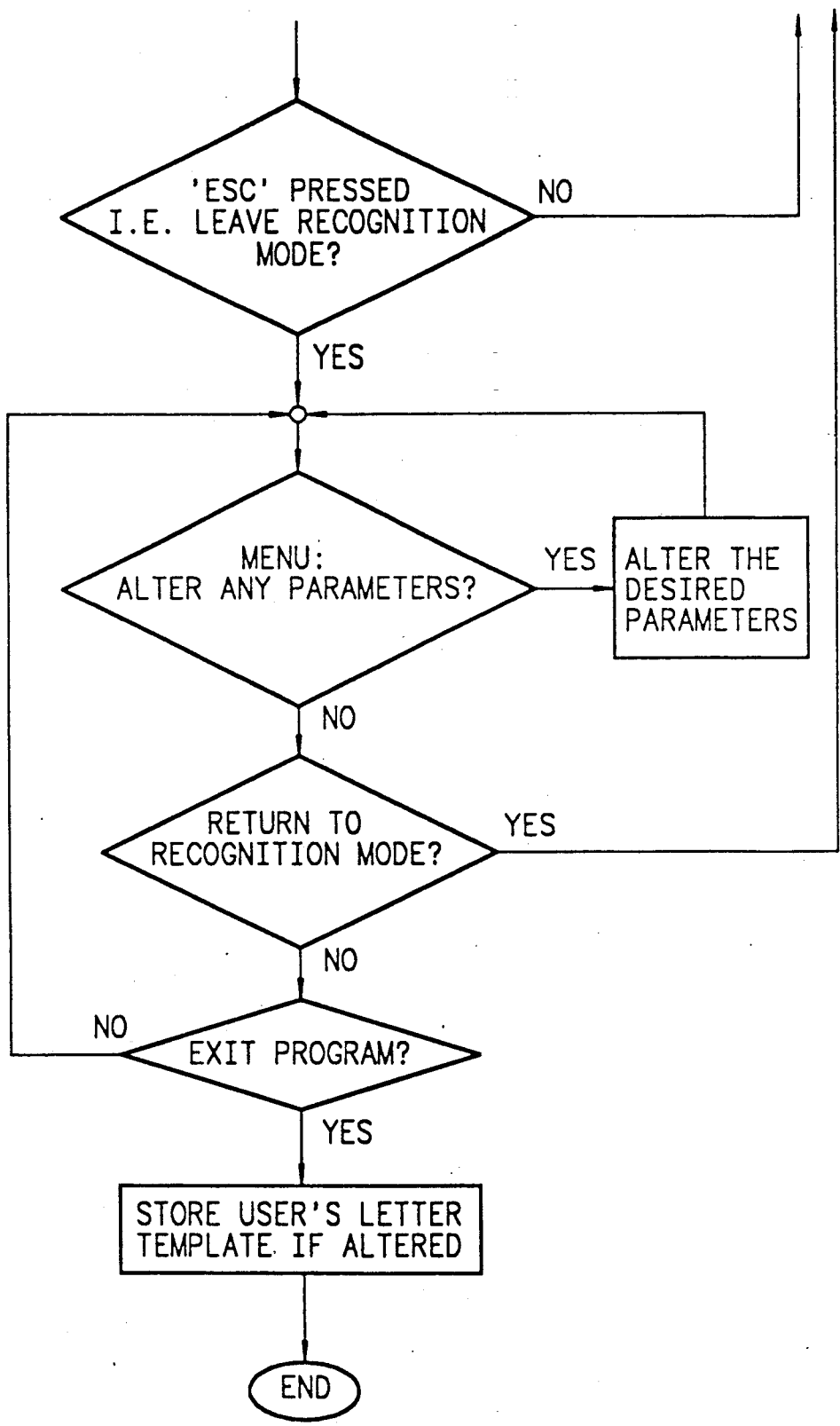

FIGS. 8A and 8B are a flow diagram of the letter recognition algorithm software running on the IBM AT computer.

Figure 9:
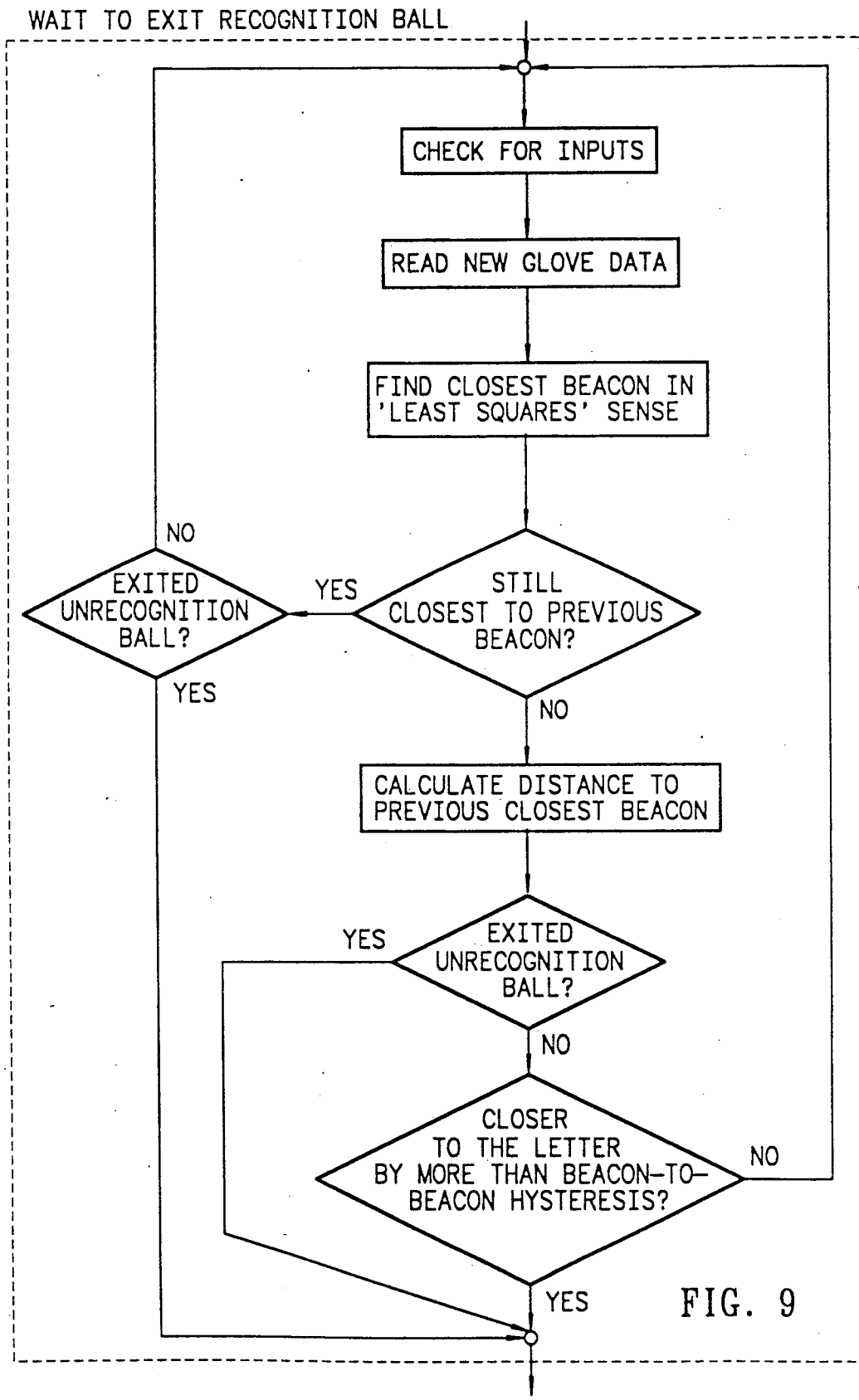
FIG. 9 is a flow diagram of a Wait to Exit recognition ball routine in the flow diagram of FIGS. 8A and 8B.
Figure 10:
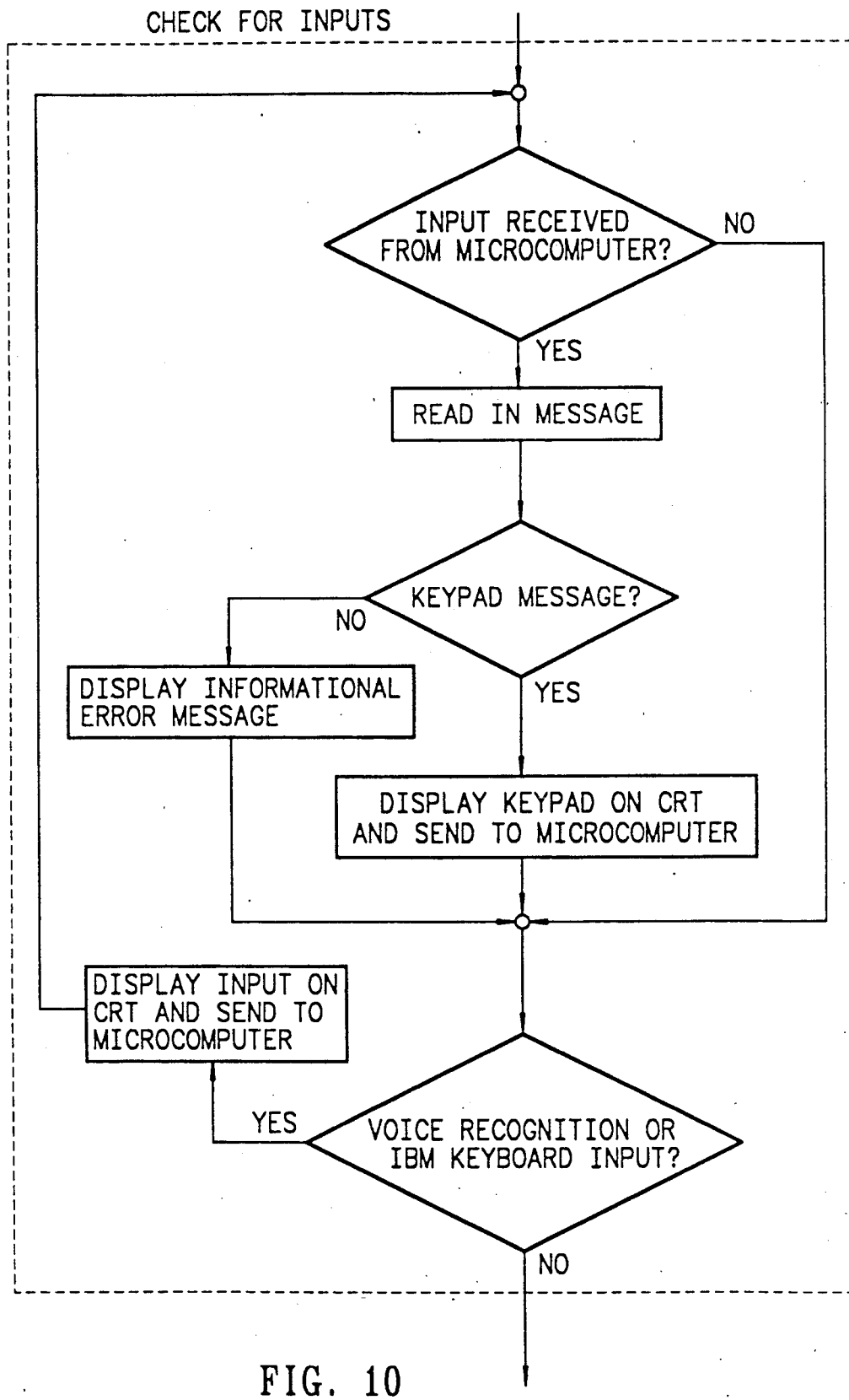
FIG. 10 is a flow diagram of a Check for Inputs routine in the flow diagram of FIGS. 8A and 8B.

FIG. 9 is a flow diagram of the Wait to Exit recognition ball routine and FIG. 10 is a flow diagram of the Check for Inputs routine as used in the letter recognition algorithm of FIGS. 8A and 8B. FIG. 11 is a flow diagram of the I/O and sampling software running on the Motorola microcomputer.

A printout of the software illustrated in FIGS. 8A, 8B, 9, and 10, written in Turbo Pascal, is attached hereto and incorporated by reference. A printout of the software illustrated in FIG. 11, written in Forth, is also attached hereto and incorporated by reference.

Referring now to FIG. 8A, the flow diagram for the letter recognition algorithm software begins with the initialize/alter default recognition parameters at 50. These parameters include the following:

1. recognition/unrecognition ball radii
2. beacon-beacon hysteresis margin that permits unrecognition if "substantially closer" to a new beacon
3. recognition confidence margin, required to recognize one beacon over the next nearest neighbor
4. recognition sampling period
5. maximum velocity that can denote a pause
6. number of sample points required to abide by parameters (1), (3) and (5), supra
7. joint weighting
8. Additional letter 'c' recognition pause to prevent incorrect recognition
9. voice selection (e.g. male, female, child)
10. select Dexter (mechanical fingerspelling hand) on/off
11. user name selection Next, the user's hand formation template, to be used during recognition, is loaded at 52. If the user is new to the system, then a default template is loaded. The hand formation template can be altered at 54 if desired by the user forming each of the letters and symbols sequentially and recording the sensor data corresponding to each letter beacon location.

Next, all variables are reset at 56 and then the Fetch Gesture routine is activated.

Determination of a pause at a beacon is made at 58. True, the following three questions must answer true: (1) pause? (2) inside a recognition ball? and (3) closer to the closest beacon than to the second closest beacon by more than the recognition confidence margin? If Paused, then the Wait to Exit recognition ball routine (FIG. 9) is activated. If not paused, then the Check for Inputs routine (FIG. 10) is implemented. Next, previous sensor data values are shifted back in time one sample period prior to reading current sensor data to be used to recognize a new beacon for readout and storage. New glove data is read and the closest beacon is then determined using a "Least Squares" (L.S.) mathematical determination in 62. The Find Closest Beacon routine, 62, has been optimized to very quickly search through all the possible beacons and record the closest and second-closest beacons. The quick search is achieved by first calculating the least squares distance to the previous closest and second-closest beacons. The remaining letter beacon distances are calculated in order of decreasing probability as determined from letter probabilities of the English language. Since the least squares method involves summing up the squares at the deviations of the selected beacon's joint sensor value from the corresponding current hand-state's joint sensor value, the calculation is checked after each squared deviation is added to the running total. If the intermediate sum is already greater than the previous second-closes beacon, the L.S. distance calculation for that beacon is terminated and the next beacon's distance determination is begun. In many cases, the previous closest and second-closest beacons will again be the new closest and second-closest beacons, so after the L.S. distances to these previous closest beacons has been calculated, only the first term in the L.S. sum of the remaining beacon distances will need to be calculated. If the new closest beacons are not the previous closest beacons, the search algorithm calculates the beacon distances in order of decreasing probability so that as many of the following distance calculations as possible can be terminated prematurely. Thus, computation time is dramatically reduced.

If it is determined from the new glove data that the user has not paused at a beacon, then a recognition delay is performed and new glove data is again read using the cycle described above. If it is determined from the new glove data that the user has paused at a beacon, then the letter corresponding to the beacon is displayed on the IBM monitor and then sent to the microcomputer for processing and display on the various peripheral devices shown in FIG. 7. Thereafter, the flow diagram proceeds to FIG. 8B where an escape variable is tested. If the escape variable tests negative, then the main recognition loop is repeated and new glove data is read. If the escape variable tests positive, then the recognition loop is exited. Thereafter, the user can choose to alter recognition parameters, return to the recognition loop, or exit the program. If it is desired to exit the program, the user's letter beacon template is stored to hard disk to be retrieved later at 52 when the program is restarted.

FIG. 9 is a flow diagram for the Wait to Exit recognition ball routine. After checking for inputs and reading the new glove data to determine a new hand-state position, the closest beacon is determined by using the numerical method of Least Squares. If the new hand state is still "closest" to the previously recognized beacon, then it is determined whether the unrecognition ball of the previous beacon has been exited. If not exited, the Wait to Exit recognition ball routine is started again. If it is determined that the unrecognition ball of the previous beacon has been exited, the Wait to Exit recognition ball routine, is exited, returning control to the main program at 60 (FIG. 8A). If the new hand state is not closest to the previous beacon, then a calculation is made of the distance to the previous closest beacon. If the new hand state has exited the previous beacon's unrecognition ball then the Wait to Exit recognition ball routine is exited and a new beacon can be recognized. However, if the new hand state has not exited the unrecognition ball of the previous beacon, then it is determined whether the new hand state is closer to a new letter beacon by more than the beacon-to-beacon hysteresis margin. If yes, the Wait to Exit recognition ball routine is exited. If no, the Wait to Exit routine is repeated.

FIG. 10 is a flow diagram of the Check for Inputs routine. Basically the routine is looking for an input received from the microprocessor, a keypad message, voice recognition or IBM keyboard input. If such messages are present, then they are displayed.

Figure 11A:
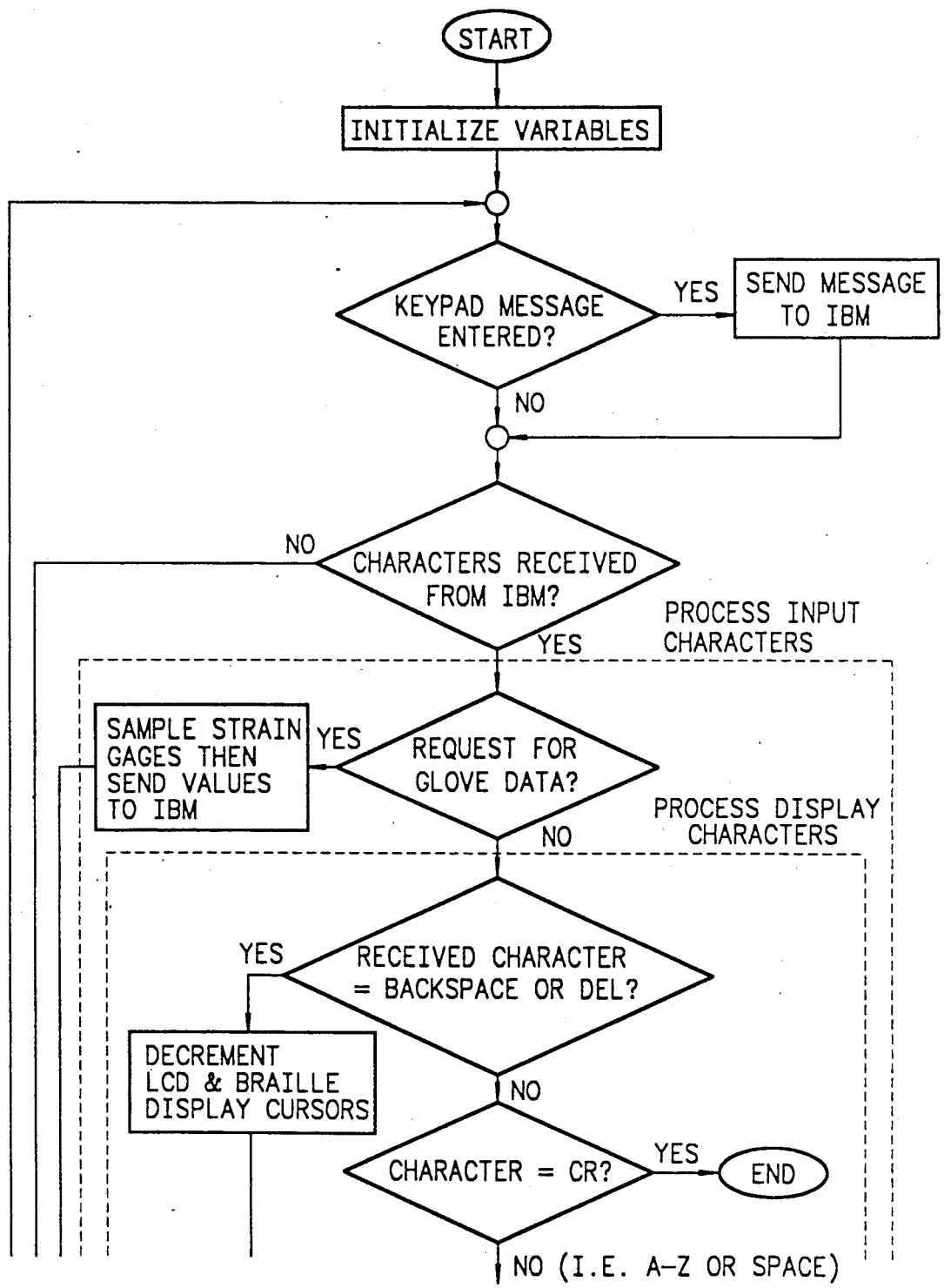
FIGS. 11A and 11B are a flow diagram of an I/O and sampling software in the system of FIG. 7.
Figure 11B:
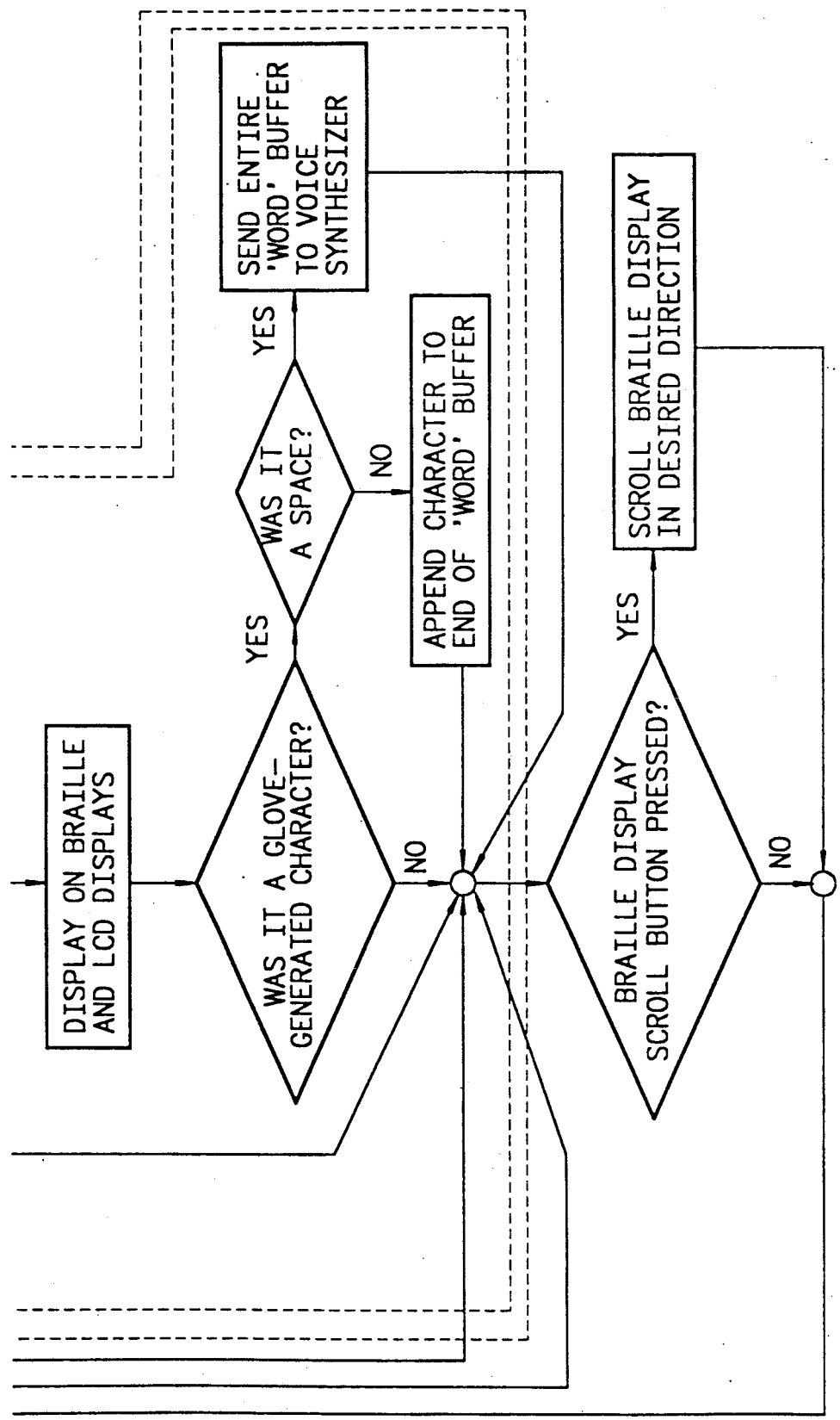

FIGS. 11A and 11B are a flow diagram of the peripheral control and sensor sampling routine running on the Motorola microcomputer. Basically, the routine communicates with the IBM computer and controls the operation of peripheral devices shown in FIG. 7.

The instrumented glove and communication system in accordance with the invention offer distinct advantages over known prior-art communication systems. The instrumented glove utilizes linear sensors and is insensitive to bend radius and joint coupling. Importantly, the glove is easily and inexpensively manufactured. The use of annealed, high-elongation strain gages in extremely thin and flexible sensors ensures that maximum stress seen by the gages is below acceptable limits. The glove and communication system provide a finger-spelling-to-speech system heretofore unavailable. The system enables a non-vocal person to "talk" with several hearing or deaf individuals simultaneously. The adaptive letter recognition algorithm is reprogrammable using "soft" decisions. The several peripheral output devices enable communication with vocal, non-vocal, deaf and deaf-blind individuals.

While the invention has been described with reference to specific embodiments, the description is illustrative of the invention and is not to be construed as limiting the invention. For example, the instrumented glove can be used as an input device in other man-machine environments such as in the control of robotic devices, as a cursor controller, and in artificial limb control, for example. Additionally, the strain gage sensor in accordance with the invention can be used in other garments and support structures for use by humans, other animals, and even inaminate objects. Thus, various modifications and amplifications may occur to those skilled in the art without departing from the true spirit and scope of the invention as defined by the appended claims.

We claim:

1. An instrumented glove for use in a man-machine interface comprising a cover material configured to fit on the hand of a wearer, a plurality of variable resistance strain gage means supported by said cover material and positioned to flex with movement of the hand, said cover material including guiding pockets in which said strain gage means are supported, said strain gage means comprising strain gage responsive means mounted on a flexible support material, and means electrically connected to said plurality of strain gage means for transmitting changes in resistance of said plurality of strain gage means to circuitry of the machine system.

2. The instrumented glove as defined by claim 1 wherein each of said strain gage means comprises a support material and first and second strain gage responsive means on opposing sides of said support material, whereby flexure of said strain gage means flexes said first strain gage responsive means in compression and flexes said second strain gage responsive means in tension, and means electrically connected to said plurality of strain gage means for transmitting changes in resistance of said plurality of strain gage means to the circuitry of the machine system.

3. The instrumented glove as defined by claim 2 and further including means for serially connecting said first and second strain gage responsive means whereby said first and second strain gage responsive means can function as two legs in a bridge circuit.

4. The instrumented glove as defined by claim 1 wherein said glove exposes portions of the wearer's fingers.

5. The instrumented gloves as defined by claim 1 wherein said glove exposes a portion of the wearer's palm.

6. The instrumented glove as defined by claim 3 wherein each strain gage sensor means is provided in a multiplexed Wheatstone bridge configuration.

7. An instrumented glove according to claim 1, wherein said variable resistance strain gage means comprises straight strain gage responsive means.

8. A communication system for use by deaf, deaf-blind or non-vocal individuals comprising means for deriving electrical signals indicative of the configuration of a hand of a first individual including an instrumented glove having a cover material configured to fit on the hand of a wearer, a plurality of variable resistance strain gage sensor means supported by said cover material and positioned to flex with movement of the hand, said cover material including guiding pockets in which said strain sensor means are supported, and means for electrically connecting said plurality of strain gage means to circuitry of the communication system, computer means for receiving the electrical signals and determining letters corresponding to configurations of the hand, said computer means including an adaptive pattern recognition algorithm responsive to hand-state vectors for recognizing letter beacons in hand-space, and first output means responsive to said computer means for providing an output of letters recognized by said adaptive pattern recognition algorithm.

9. The communication system as defined by claim 8 and further including a portable keyboard means for providing inputs to said computer means, second output means responsive to said computer means for providing an output to said first individual whereby a second individual can communicate with said first individual through said keyboard means.

10. The communication system as defined by claim 9 wherein said first output means includes a voice synthesizer.

11. The communication system as defined by claim 10 wherein said second output means includes a liquid crystal display.

12. The communication system as defined by claim 10 wherein said second output means includes a braille display.

13. The communication system as defined by claim 9 wherein said first output means includes a liquid crystal display.

14. The communication system as defined by claim 13 wherein said second output means includes a liquid crystal display.

15. The communication system as defined by claim 13 wherein said second output means includes a braille display.

16. The communication system as defined by claim 8 wherein each of said strain gage means comprises a support material and first and second strain gage responsive means on opposing sides of said support material, whereby flexure of said strain gage means flexes said first strain gage responsive means in compression and flexes said second strain gage responsive means in tension.

17. The communication system as defined by claim 13 and further including means for serially connecting said first and second strain gage responsive means whereby said first and second strain gage responsive means can function as two legs in a bridge circuit.

18. The communication system as defined by claim 8 wherein each of said letter beacons includes a recognition hypersphere in hand-space in which the corresponding letter is recognized.

19. The communication system as defined by claim 18 wherein each of said letter beacons includes a second hypersphere outside of said recognition hypersphere which a hand-state vector must leave after the corresponding letter has been recognized before the corresponding letter can again be recognized.

20. The communication system as defined by claim 19 wherein said adaptive pattern recognition algorithm detects reduced hand-state velocity and there determines the nearest letter beacon to a hand-state vector.

21. The communication system as defined by claim 20 wherein the nearest letter beacon is determined by Least Squares distance.

22. The communication system as defined by claim 21 wherein the hand-state vector can be within the recognition hypersphere of both the nearest letter beacon and the second-nearest letter beacon.

23. The communication system as defined by claim 21 wherein recognition is permitted when the least squares distance from the hand-state vector to the nearest letter beacon is less than the least squares distance from the hand-state vector to the second closest letter beacon by more than a recognition confidence margin.

24. The communication system as defined by claim 21 wherein the currently recognized letter beacon is unrecognized whenever the least squares distance from the hand-state vector to any letter beacon is less than the least squares distance from the hand-state vector to the currently recognized letter beacon by more than a beacon-to-beacon hysteresis margin.

25. The communication system as defined by claim 21 wherein the search order calculation for determining the next nearest letter beacon starts by calculating the least squares distance to the most recent nearest letter beacon, then calculates the least squares distance to the most recent second nearest letter beacon, and then proceeds by checking the remaining letter beacons in order of decreasing probability of occurrence, where each least squares distance calculation is prematurely terminated whenever the running sum total of the squares of individual joint errors exceeds the calculated least squares distance from the hand-state to the current second closest letter beacon.

* * * * *